United States Patent
Hess et al.

(10) Patent No.: US 7,545,915 B2
(45) Date of Patent: Jun. 9, 2009

(54) DOSE RATE CONTROL IN AN X-RAY SYSTEM

(75) Inventors: Robert Hess, Hasloh (DE); Reinhard Steiner, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 5 days.

(21) Appl. No.: 11/815,666

(22) PCT Filed: Feb. 2, 2006

(86) PCT No.: PCT/IB2006/050354
§ 371 (c)(1),
(2), (4) Date: Aug. 7, 2007

(87) PCT Pub. No.: WO2006/085247
PCT Pub. Date: Aug. 17, 2006

(65) Prior Publication Data
US 2008/0253532 A1    Oct. 16, 2008

(30) Foreign Application Priority Data
Feb. 11, 2005  (EP)  .................................. 05101011

(51) Int. Cl.
*H05G 1/44*    (2006.01)

(52) U.S. Cl. ........................ 378/108; 378/97
(58) Field of Classification Search ................... 378/16, 378/97, 108–112, 65, 37
See application file for complete search history.

(56) References Cited

U.S. PATENT DOCUMENTS

| 4,501,010 | A | 2/1985 | Grassme | |
|---|---|---|---|---|
| 6,490,337 | B1 * | 12/2002 | Nagaoka et al. | 378/20 |
| 6,754,307 | B2 * | 6/2004 | Brendler et al. | 378/108 |
| 2003/0012340 | A1 * | 1/2003 | Chornenky | 378/122 |

FOREIGN PATENT DOCUMENTS

| DE | 2855405 | 10/1980 |
|---|---|---|
| WO | 9900054 | 1/1999 |

* cited by examiner

*Primary Examiner*—Hoon Song

(57) ABSTRACT

A controller for controlling the dose rate (exposure kV tube voltage) of an X-ray system, in which the actual dose rate is measured and compared with an optimal dose rate, and the resultant difference value is fed to a module (20) (e.g. a PID module) which is arranged to adjust the dose rate (by adjusting the exposure kV voltage) so as to minimize the difference value. No preset parameters are required to be entered prior to exposure.

14 Claims, 4 Drawing Sheets

DOSE RATE CONTROL IN AN X-RAY SYSTEM

This invention relates generally to a method and device for controlling the dose rate of an X-ray tube in an X-ray imaging system.

It is widely known, in the field of non-invasive medical diagnosis, to obtain a radiation image of a subject to be imaged with radiation and detecting the intensity distribution of the radiation that has been transmitted through the subject to be imaged.

Referring to FIG. 1 of the drawings, there is illustrated schematically a typical X-ray system which comprises an X-ray image detecting sensor unit 3 having a plurality of photoelectric conversion elements. An X-ray source 2, fed by an X-ray generator comprising a high voltage generator 5, generates X-rays that are transmitted through a subject 4 to the sensor unit 3, the photoelectric conversion elements of which generate an image signal representative of the intensity distribution of the radiation transmitted through the subject 4. The image signal is fed to a digital image processing means within a control unit 6 and the resultant image is then displayed.

In conventional systems, for X-ray examination of the human body and its organs, it is necessary to perform a number of pre-setting operations in respect of the X-ray generator so as to achieve an optimum exposure of an examination zone. This is due to the fact that the density of the various organs or regions of the body is very different per se and also differs from one person to another, i.e. in dependence on the size and weight of the subject to be imaged. More specifically, the following parameters in particular can be adapted so as to achieve the desired exposure in each case.

On the one hand, the dose rate of the X-ray tube (that is, essentially, the exposure kV voltage) determines the contrast and the contrast range of the objects imaged. The radiation dose, on the other hand, determines the signal-to-noise ratio of the image and the exposure time determines the sharpness of the image, and all of these should ideally be optimised for the subject to be imaged (i.e. taking into account the thickness of the subject to be imaged), whilst applying as small as possible radiation dose in order to ensure as safe as possible examination of the subject.

In a typical X-ray system, a user is provided with a number of options to preset the above-mentioned parameters based on various combinations of examination type, e.g. hip, skull axial, etc. and patient thickness. Each preset option, of which there may be hundreds, has associated therewith a data set including tube voltage and tube current for the selected option in an attempt to achieve the maximum image quality for every examination. However, the larger the number of options available, the higher the chance of selecting the wrong one, resulting in a non-optimal image quality and/or the patient being subjected to an unnecessarily high dose of radiation.

U.S. Pat. No. 6,754,307 describes an X-ray generator which includes an automatic exposure control device wherein a maximum exposure time and an exposure kV start voltage for the X-ray tube are preset, and then once the X-ray exposure has been commenced, the exposure can be automatically controlled by measuring the X-ray absorption: if the X-ray abosrption is found to be greater than some predetermined threshold, the exposure kV start voltage is adjusted at the maximum exposure time and, if the X-ray abosption is determined to be less than the above-mentioned threshold, the exposure time is adjusted, whilst maintaining a constant exposure kV start voltage.

A variation on this system is known which adjusts the preset tube voltage within a certain window. The operator selects an examination type to give an underlying tube voltage and current. When the operator presses a release button, the exposure will start as expected with the preset tube voltage and current settings. However, within the first one or two milliseconds of exposure, the system measures the dose rate and estimates the expected length of exposure. If it turns out that the exposure time will be too long or too short, the tube voltage wilk1 be adjusted upward or downward respectively, as required.

Thus, in conventional X-ray systems, the tube voltage is preset via the user interface and a large number of present combinations provided by the system. The above-mentioned known system adjusts the tube voltage during exposure to a certain extent, but the voltage will be kept close to the preset value such that it does not effectively compensate for the case where an error has been made in selecting the initial preset combination.

Thus, it is an object of the present invention to provide a controller for an X-ray system which may be used to adjust the dose rate (i.e. the exposure kV (tube) voltage) for any patient thickness (e.g. 1 to 50 cm) within the full kV range (e.g. 40 to 150 kV) within a single exposure, without any preset knowledge of the patient or examination type.

In accordance with the present invention, there is provided a controller for an X-ray system comprising an X-ray generator, feeding an X-ray tube for generating X-radiation and means for detecting the intensity distribution of the X-radiation that has been transmitted through a subject to be imaged, said controller comprising means for determining an actual dose rate at which said X-radiation is generated, comparing said actual dose rate with a predetermined optimal dose rate dependent on the thickness of said subject and adjusting said actual dose rate to substantially correspond with said optimal dose rate.

Also in accordance with the present invention, there is provided a method of controlling the dose rate in an X-ray system comprising an X-ray generator feeding an X-ray tube for generating X-radiation and means for detecting the intensity distribution of the X-radiation that has been transmitted through a subject to be imaged, said method comprising determining an actual dose rate at which said X-radiation is generated, comparing said actual dose rate with a predetermined optimal dose rate dependent on the thickness of said subject and adjusting said actual dose rate to substantially correspond with said optimal dose rate.

Thus, the present invention effectively provides an automatic tube voltage control which enables an optimal image quality to be automatically obtained in respect of every examination, at a minimum radiation dose, leaving the radiologist free to concentrate on the diagnosis.

Preferably, the actual dose rate is adjusted by adjusting the exposure kV voltage of said X-ray generator.

Means may be provided for storing predetermined values of optimal dose rate per tube current as a function of tube voltage and means for multiplying an actual tube current supplied to said X-ray tube by said X-ray generator to determine an optimal dose rate in respect of said subject. A difference value between said optimal dose rate and said actual dose rate may be determined, and the difference value may be fed to a (e.g. PID) module, the output of which is used to control the exposure kV voltage of said X-ray tube. In one exemplary embodiment, an actual dose rate substantially equal to said optimal dose rate for said subject is obtained by minimising said difference value.

The optimal dose rate may be compensated for source image distance (SID).

The controller may further comprise X-ray dose control means.

The thickness of the subject to be imaged may be based on the water equivalent thereof.

The present invention extends to an X-ray system comprising an X-ray generator feeding an X-ray tube for generating X-radiation, means for detecting the intensity distribution of the X-radiation that has been transmitted through a subject to be imaged, and including a controller as defined above.

These and other aspects of the present invention will be apparent from, and elucidated with reference to, the embodiment described herein.

An embodiment of the present invention will now be described by way of example only and with reference to the accompanying drawings, in which.

As mentioned, it is assumed for the purposes of the following exemplary embodiment of the present invention, that there is an optimal tube voltage for each patient thickness and examination type. The values are optimised in terms of maximum image quality and minimum patient dose. The large number of examination types may be sorted in groups for bones, thorax, abdomen, radiopaque material etc. Within a group the examination types vary only in patient thickness and, hence, may be plotted in a diagram. The knowledge of the optimal tube voltage may also be used the other way round: A given tube voltage produces the best image quality only for a particular patient thickness.

Figure 1:
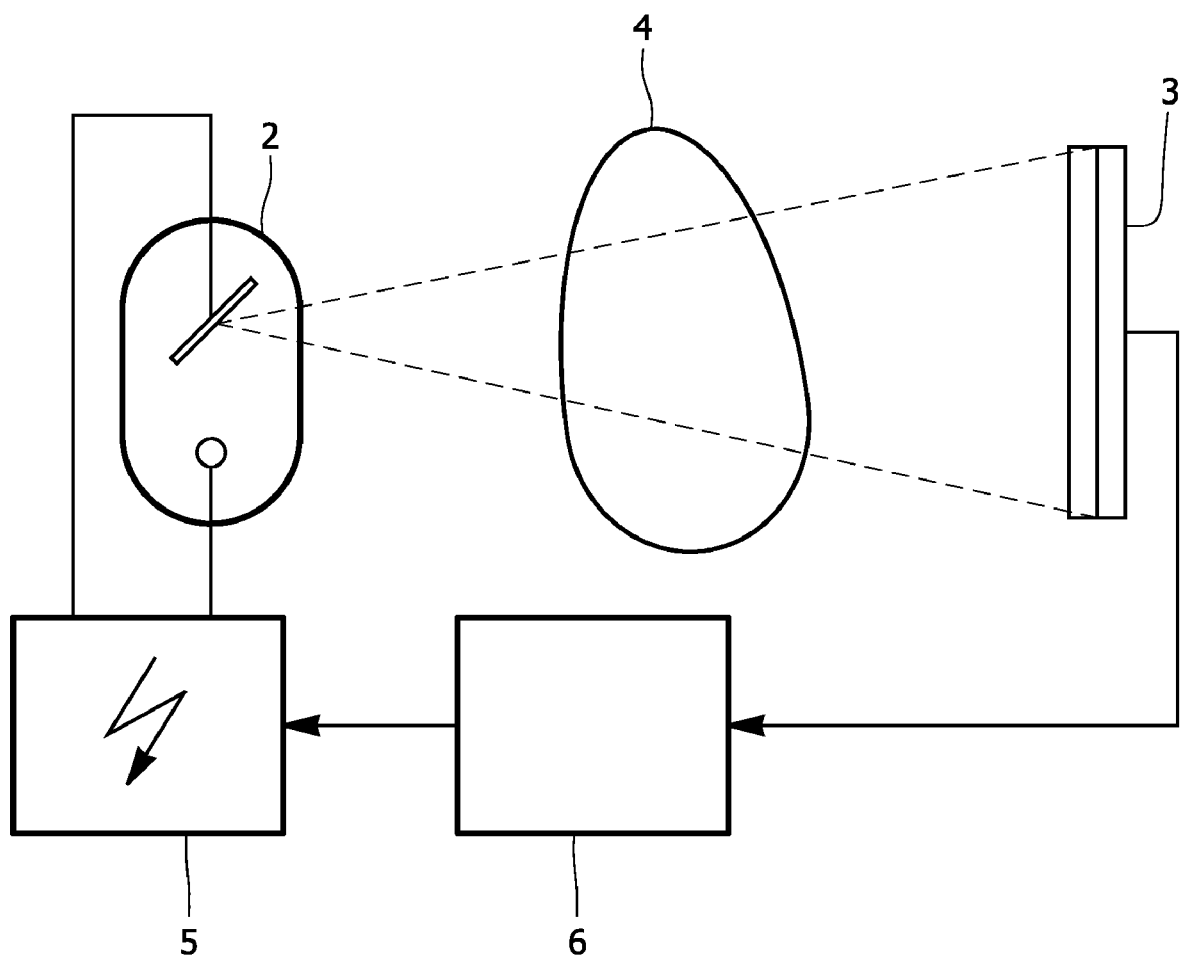
FIG. 1 is a schematic diagram illustrating a typical X-ray system.
Figure 2:
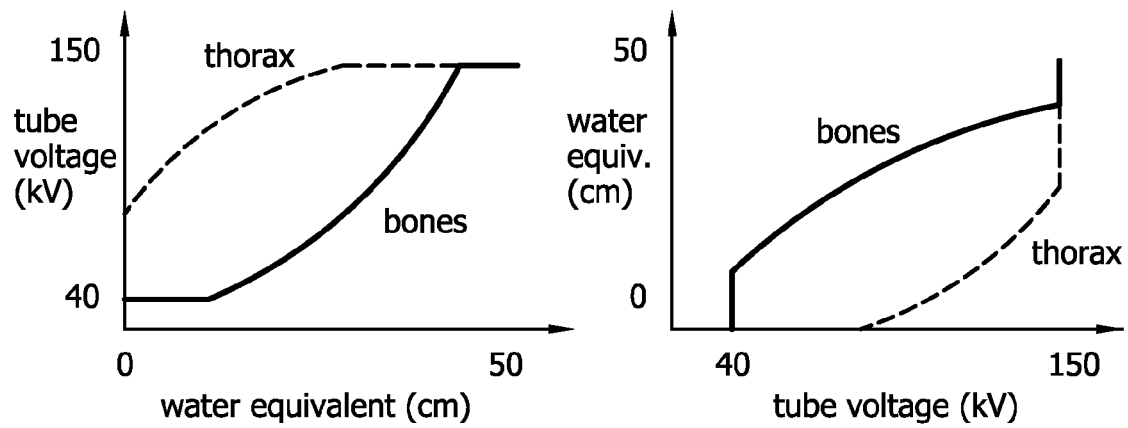
FIG. 2 illustrates graphically an example of optimal tube voltages relative to the water equivalent of a patient and the inverse graph thereof.

FIG. 2 shows, on the left, two principle examples of the optimal tube voltage. Depending on the type of examination, the shape of curves may vary. For example, a thorax examination requires a much higher voltage than an examination where bones are of interest. Since the patients vary in density, the data is plotted against the water equivalent instead of the patient thickness. The right hand diagram in FIG. 2 is the inversion of the left-hand one. It illustrates the patient thickness corresponding to which the given tube voltage would lead to the best image quality.

Figure 3:
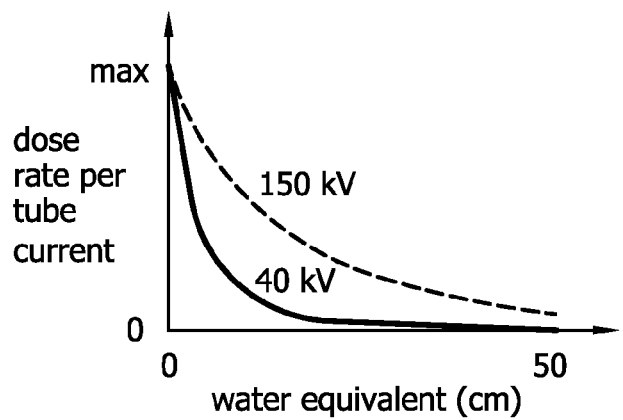
FIG. 3 illustrates typical dose rates against patient thickness for two tube voltages.

It is possible to evaluate the dose rate behind the patient as a function of patient thickness, tube voltage and tube current. Since the dose rate is proportional to tube current it is only necessary to evaluate the dose rate per tube current as a function of patient thickness and tube voltage. Again, the patient thickness should be treated in terms of water equivalent. FIG. 3 shows dose rates per tube current for two tube voltages. The principle data are normalised to the dose rate at 0 cm.

Figure 4:
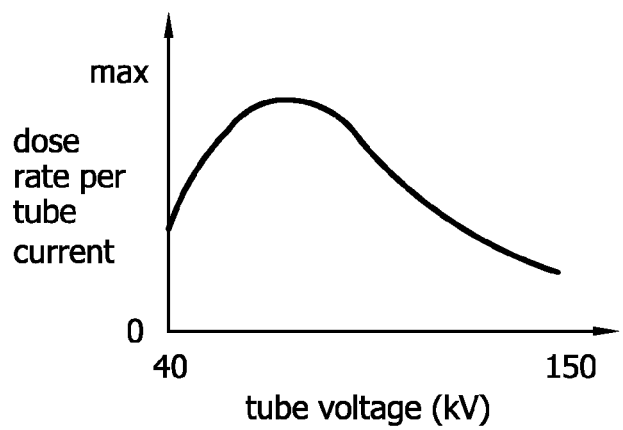
FIG. 4 illustrates graphically the dose rate per tube current for patient thickness by which the given tube voltage is the optimum.

The curves in FIG. 2 and FIG. 3 may be put together in a graph showing the dose rate per tube current behind the patient with optimal thickness as a function of the tube voltage. A point in the left diagram in FIG. 2 gives a pair of tube voltage and patient thickness. These two values may be used as an input in FIG. 3 to gain the dose rate per tube current behind the patient. FIG. 4 shows an example of this diagram. A point of this curve at tube voltage $V_I$ gives the dose rate per tube current behind the patient with a thickness by which $V_I$ is the optimal voltage.

This curve is the major input for the tube voltage control mechanism in accordance with an exemplary embodiment of the invention.

Figure 5:
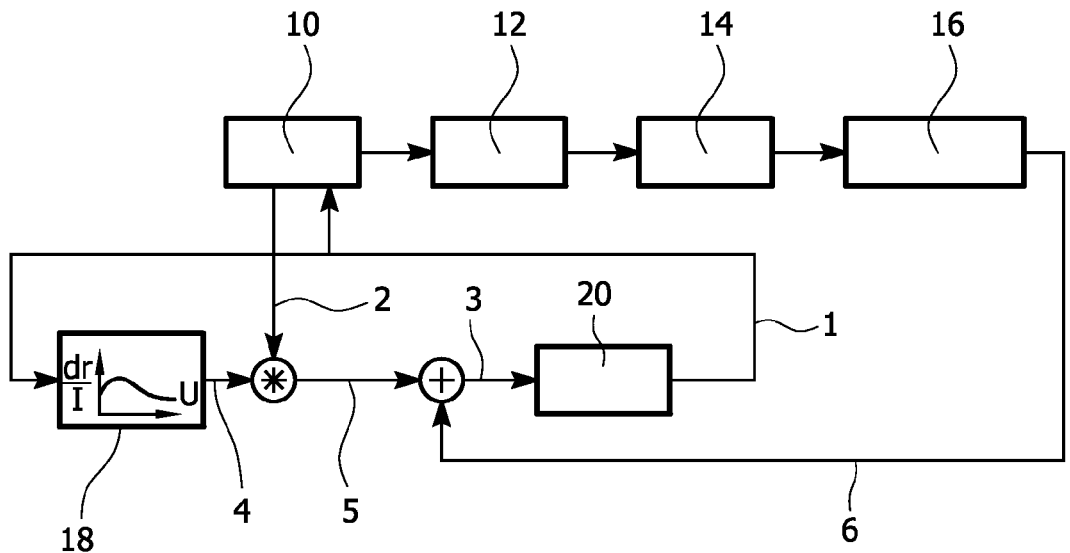
FIG. 5 is a schematic block diagram illustrating a controller according to an exemplary embodiment of the present invention.

FIG. 5 shows a block diagram of a controller according to an exemplary embodiment of the present invention, for adjusting the tube voltage to its optimum. The four blocks in the top row illustrate the elements of the forward path. The generator 10 receives a request for a certain tube voltage and supplies the X-ray tube 12 with this voltage. The X-ray tube 12 sends a large number of photons towards the patient 14 and some of them (plus some secondary photons) will leave the patient on the other side. The dose rate sensor 16 detects the transmitted photons and generates a voltage that is proportional to the dose rate behind the patient 14.

The feed back loop needs three signals: the measured dose rate ⑥, the actual tube current ② and the tube voltage (D. The function block 18 on the left-hand side converts the actual tube voltage ① to the so-called optimal dose rate per tube current ④, which a patient with thickness optimal to this voltage would produce (see also FIG. 4). If the optimal dose rate per tube current ④ is then multiplied by the actual tube current ②, the optimal dose rate ⑤ is obtained. The difference between the optimal dose rate ⑤ and the measured dose rate ⑥ from the forward path is the delta dose rate ③. The delta dose rate passes through a PID module 20 to adjust the tube voltage ①. The PID module 20 has a Proportional, an Integrating and a Differentiating part. Also, a delay element of first or second order may be required to stabilize and speed up the regulation loop. In a simplified model the PID module 20 is a simple integrator.

If a patient is too thick for the actual tube voltage the measured dose rate ⑥ will be less than expected, and the delta dose rate ③ will be positive which will lead to an increase of the tube voltage ①. On the other hand, if for a given tube voltage the patient is too thin, the measured dose rate ⑥ will be higher than the desired one, and the delta dose rate ③ will be negative, hence, the tube voltage ① will decrease.

At the beginning of an exposure the desired tube voltage should not be set to an average value like 75 kV but rather the lowest possible value of the chosen examination type, e.g. 40 kV for bones and 80 kV for lungs. This is because for very thin patients (pediatric) the doses are so small, that there will not be enough time to regulate the tube voltage down within the first 10% of the dose. Whereas for thick patients the overall dose is higher, and there is sufficient time to adjust the voltage upward.

The following description focuses first on the dose rate curve for the optimal patient thickness (see FIG. 4), following which the timing of the regulation loop is briefly discussed.

Figure 6:
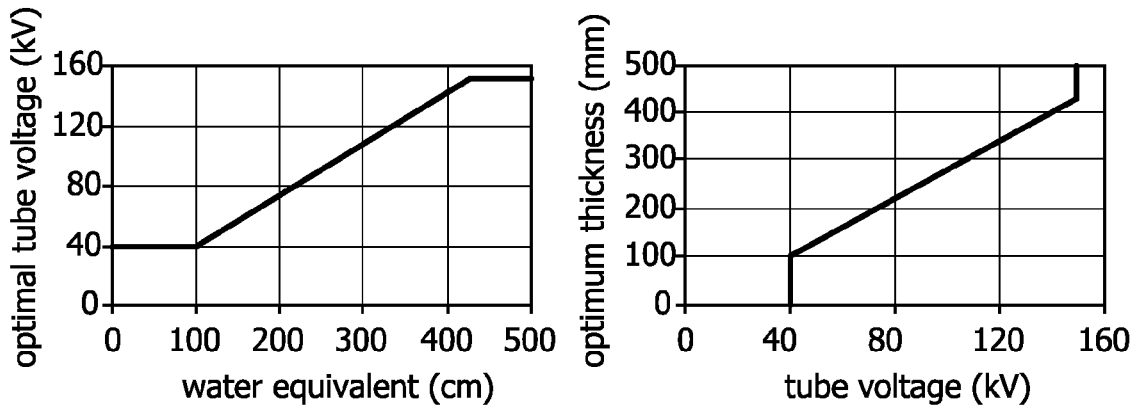
FIG. 6 illustrates graphically, by way of example, optimum tube voltage as a function of patient thickness for bones.

As an example, assume an optimisation curve as illustrated on the left side in FIG. 6. This curve could be true if the radiologist is interested in any soft of bones. For patients or parts of the body with thickness below or equal to 10 cm the recommended tube voltage would then be 40 kV and above 43 cm 150 kV. The gap between 10 and 43 cm is filled by a linear interpolation.

The left graph in FIG. 6 may be read the other way around: What is the optimal patient thickness, by which the given tube voltage leads to the maximum image quality? The right graph in FIG. 6 is simply the reverse of the left graph.

Figure 7:
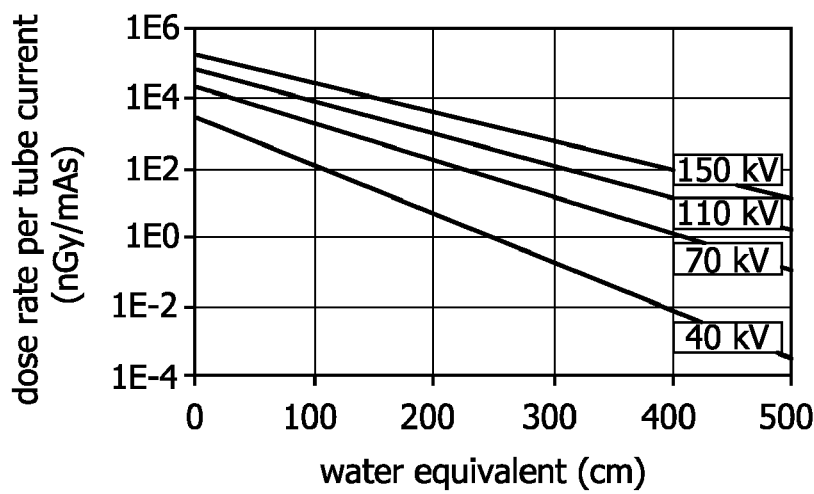
FIG. 7 illustrates graphically, by way of example, dose rate per tube current in respect of water.

Independent of the examination type it is possible to evaluate dose rate per tube current behind the patient as a function of tube voltage and patient thickness. This is true for a given geometry and a defined filter set. An increase of source image distance, SID will have a quadratic influence, whereas a change of the pre-filter requires a new evaluation of the data. The graph in FIG. 7 is based on simulation of a typical X-ray tube (SRO 33100-ROT 350) with no extra pre-filter and with an SID of 1 m.

Figure 8:
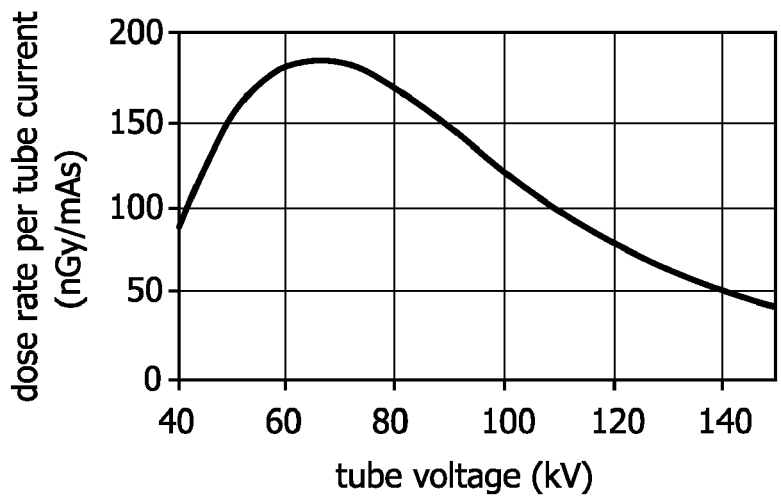
FIG. 8 illustrates graphically, by way of example, dose rate per tube current behind a patient for optimal patient thickness as a function of tube voltage.

Now the graphs may be put together to gain the dose rate per tube current behind the patient for the optimal patient thickness as a function of the tube voltage, see FIG. 8.

The forward path of the regulation loop in FIG. 5 has a certain time delay. If the generator is requested to increase the tube voltage there is a delay until the tube really has this voltage. The delay of the X-ray tube and the transmission of photons through the patient lie in the range of nanoseconds and, hence, may be neglected. But then the dose rate sensor has again a delay.

The target is to regulate the delta dose rate ③ (see FIG. 5) to zero in a very short time. Therefore the forward path must be examined thoroughly to gain input for the optimisation of the PID module.

The forward path is not linear, hence, an optimal PID module is also non-linear. In modern systems the dost control loops are controlled by a digital signal processor (DSP). In such systems it is possible to compensate non-linear effects of the forward path.

The overall dose control is not shown in the block diagram in FIG. 5, which only illustrates the tube voltage control. The dose control will be implemented in the standard way, e.g. with an amplimat chamber or a photodiode behind an image intensifier.

Figure 9:
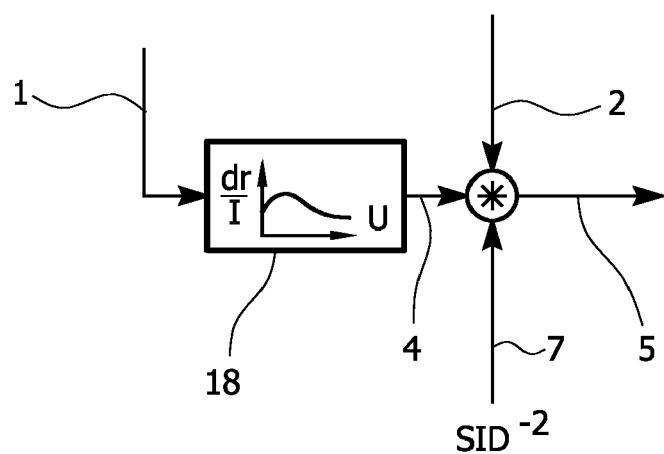
FIG. 9 is a schematic block diagram of a portion of the controller of FIG. 5, including compensation for source image distance (SID).

The intensity of a point source depends on the distance by the inverse square law. For systems with a variable geometry the SID must be taken into account. The way to calculate the dose signals for an SID of 1 m, and then to divide the dose value by the square of the actual SID. FIG. 9 shows a part of the block diagram in FIG. 5 including the influence of the source image distance.

If the dose rate for the optimal patient ④ has been calculated for an SID of 1 m, then the result must be divided by the square of the actual SID in m² ⑦ to gain the dose rate for the current setting.

The automatic voltage control over the full kV range may be applied to all medical X-ray systems for single exposures (typically radiographic systems, but also Universal Radiographic, Fluoroscopic and Surgery systems as well as Cardiac and Vascular systems. However, a dose rate signal is required. This could be photodiode behind the image intensifier, an amplimat chamber or an integrated dose sensing layer as envisaged for more recently developed flat detectors.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A controller for an X-ray system comprising an x-ray generator for providing a tube voltage to an X-ray tube for generating X-radiation and means for detecting the intensity distribution of the X-radiation that has been transmitted through a subject to be imaged, said controller comprising:
   means for measuring a dose rate of said X-radiation,
   storage means for storing predetermined values of optimal dose rate per tube current as a function of tube voltage,
   means for measuring a tube current supplied to said X-ray tube by said X-ray generator,
   a multiplier for multiplying the tube current by a value of optimal dose rate per tube current selected from said predetermined values of optimal dose rate per tube current to determine an optimal dose rate for said subject,
   a comparator for comparing the measured dose rate with the optimal dose rate dependent on the thickness of said subject, and
   a control for adjusting the dose rate to substantially correspond with the optimal dose rate.

2. A controller according to claim 1, wherein the dose rate is adjusted by adjusting the tube voltage.

3. A controller according to claim 1, wherein said comparator comprises means for determining a difference value between said optimal dose rate and said measured dose rate.

4. A controller according to claim 3, wherein the dose rate is adjusted to minimize difference value.

5. A controller according to claim 1, wherein said optimal dose rate is compensated for source image distance (SID).

6. A controller according to claim 1, further comprising X-ray dose control.

7. A controller according to claim 1, wherein said thickness of said subject is based on the water equivalent thereof.

8. An X-ray system comprising an x-ray generator for providing a tube voltage to an X-ray tube for generating X-radiation and means for detecting the intensity distribution of the X-radiation that has been transmitted through a subject to be imaged, and further comprising a controller according to claim 1.

9. A method of controlling the dose rate in an X-ray system comprising an X-ray generator for providing a tube voltage to an X-ray tube for generating X-radiation and means for detecting the intensity distribution of the X-radiation that has been transmitted through a subject to be imaged, said method comprising:
   measuring a dose rate of said X-radiation,
   measuring a tube current supplied to said X-ray tube by said X-ray generator,
   multiplying the tube current by a value of optimal dose rate per tube current to determine an optimal dose rate for said subject,
   comparing the measured dose rate with the optimal dose rate, dependent on the thickness of said subject and
   adjusting the tube voltage to adjust the measured dose rate to substantially correspond with the optimal dose rate.

10. A method according to claim 9, comprising adjusting the dose rate by adjusting the tube voltage.

11. A method according to claim 9, wherein the step of comparing the measured dose rate with the optimal dose rate comprises determining a difference value between said optimal dose rate and said measured dose rate.

12. A method according to claim 11, wherein the dose rate is adjusted to minimize the difference value.

13. A method according to claim 9, comprising compensating said optimal dose rate for source image distance (SID).

14. A method according to claim 9, using a water equivalent of said subject for determining said thickness.

* * * * *